Figure 1:
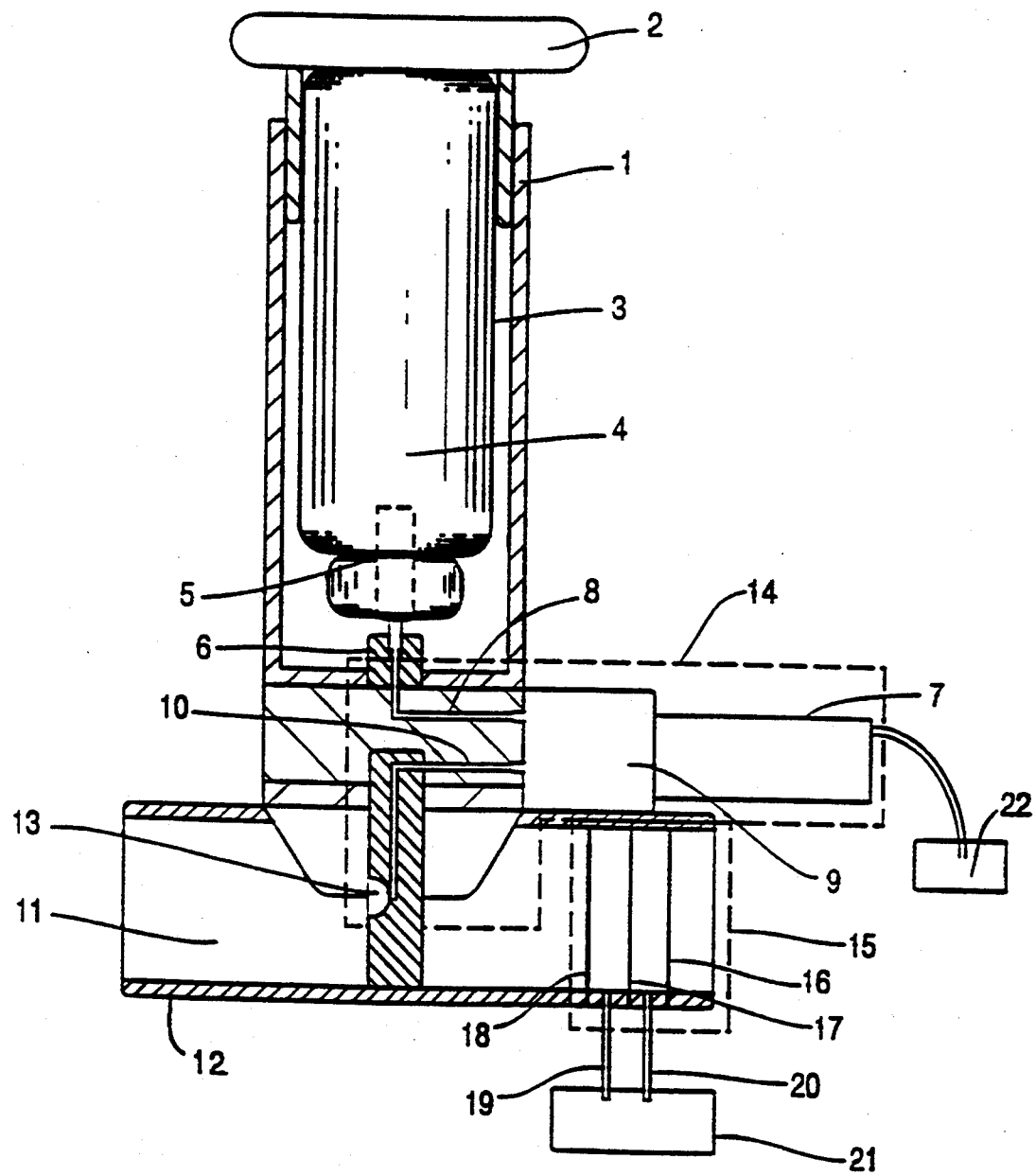

United States Patent [19]
Rubsamen

[11] Patent Number: 5,419,315
[45] Date of Patent: May 30, 1995

[54] INTRAPULMONARY DELIVERY OF HORMONES

[75] Inventor: Reid M. Rubsamen, Berkeley, Calif.

[73] Assignee: Aradigm Corporation, Hayward, Calif.

[21] Appl. No.: 279,720

[22] Filed: Jul. 25, 1994

Related U.S. Application Data

[63] Continuation of Ser. No. 10,989, Jan. 29, 1993, abandoned.

[51] Int. Cl.$^6$ ............................................. A61M 11/00
[52] U.S. Cl. .......................... 128/200.14; 128/200.23; 128/204.21; 128/204.23
[58] Field of Search ....................... 128/200.14, 200.23, 128/202.22, 203.12, 205.23, 204.21, 204.23

[56] References Cited

U.S. PATENT DOCUMENTS

| | | |
|---|---|---|
| 4,106,503 | 8/1978 | Rosenthal et al. |
| 4,604,847 | 8/1986 | Moulding, Jr. et al. |
| 4,677,975 | 7/1987 | Edgar et al. |
| 4,686,231 | 8/1987 | Bender et al. |
| 4,819,629 | 4/1989 | Jonson . |
| 4,984,158 | 1/1991 | Hillsman . |
| 5,167,506 | 12/1992 | Kilis et al. |
| 5,331,953 | 7/1994 | Anderson et al. ............. 128/200.23 |
| 5,333,106 | 7/1994 | Lanpher et al. ................ 128/200.23 |

FOREIGN PATENT DOCUMENTS

| | | |
|---|---|---|
| 0232235 | 8/1987 | European Pat. Off. |
| 0232235 | 8/1987 | European Pat. Off. |
| 2164569A | 3/1986 | United Kingdom . |
| 2164569 | 3/1986 | United Kingdom . |
| WO90/07333 | 7/1990 | WIPO . |
| WO92/07600 | 5/1992 | WIPO . |
| 9207599 | 5/1992 | WIPO ............................ 128/203.12 |
| 9207600 | 5/1992 | WIPO ............................ 128/203.12 |
| WO92/17231 | 10/1992 | WIPO . |
| 9217231 | 10/1992 | WIPO ............................ 128/200.23 |

OTHER PUBLICATIONS

Yoshida et al., "Absorption of Insulin Delivered to Rabbitt Trachea Using Aerosol Dosage Form", *Journal of Pharmaceutical Sciences*, 68(5):670–671 (1979).

Kohler, "Aerosols for Systemic Treatment", *Lung*, Suppl:677–684 (1990).

Laube et al., "Aerosolized Insulin Delivered Through the Lungs is effective in Normalizing Plasma Glucose Levels in Non–Insulin Dependent Diabetic Subjects", *Journal of Aerosol Medicine*, 4(3):286 (1991).

Colthorpe et al., "The Pharmacokinetics of Pulmonary–Delivered Insulin: A Comparison of Intratracheal and Aerosol Administration to the Rabbit", *Pharmaceutical Research*, 9(6):764–768 (1992).

Jaffe et al., "Rats Self-Administer Sufentanil Aerosol Form", *Psychopharmacology*, 99:289–293 (1989).

Smythe, "Patient-Controlled Analgesia: A Review", *Pharmacotherapy*, 12(2):132–143 (1992).

Shade, "Patient-Controlled Analgesia: Can Client Education Improve Outcomes?", *Journal of Advanced Nursing*, 17:408–413 (1992).

(List continued on next page.)

*Primary Examiner*—Edgar S. Burr
*Assistant Examiner*—Aaron J. Lewis
*Attorney, Agent, or Firm*—Karl Bozicevic; Fish & Richardson

[57] ABSTRACT

A method of treating human patients is provided by the intrapulmonary delivery of a pharmaceutically active hormone formulation. The formulation is automatically released from a hand-held, self-contained, portable device comprised of a means for automatically releasing a measured amount of drug into the inspiratory flow path of a patient in response to information obtained from a means for analyzing the inspiratory flow of a patient and after the patient is sent an audible or visual signal. Reproducible dosing is obtained by providing for automatic release in response to a measured inhalation profile. The overadministration of hormone formulations is avoided by providing a pre-programmed microprocessor designed to avoid overdosing.

13 Claims, 2 Drawing Sheets

OTHER PUBLICATIONS

Camp, "Patient–Controlled Analgesia", *AFP*, 44(6):2145–2150 (1991).

Mather, "Pharmacokinetics and Patient–Controlled Analgesia", *Acta Anaesthesiologica Belgica*, 43(1):5–20 (1992).

Ryder, "All About Patient–Controlled Analgesia", *Journal of Intravenous Nursing*, 14(6):372–381 (1991).

Rosenberg, "Patient–Controlled Analgesia", *J. Oral Maxillofac. Surg.*, 50:386–389 (1992).

Newman, *Deposition and Effects of Inhalation Aerosols* (2nd ed.), Churchill Livingstone (1983).

Gourlay et al., "Fentanyl Blood Concentration–Analgesic Response Relationship in the Treatment of Postoperative Pain", *Anesth. Analg.*, 67:329–337 (1988).

Miller, *Anesthesia* (2nd ed.), Churchill Livingstone, 1:762 (1986).

Rapp et al., "Patient–Controlled Analgesia: A Review of Effectiveness of Therapy and an Evaluation of Currently Available Devices", *DICP, The Annals of Pharmacotherapy*, 23:899–904 (1989).

Rowbotham et al., "A Disposable Device for Patient-Controlled Analgesia with Fentanyl", *Anaesthesia*, 44:922–924 (1989).

Lehmann et al., "Transdermal Fentanyl for the Treatment of Pain after Major Urological Operations",*Eur. J. Clin. Pharmacol.*, 41:17–21 (1991).

Newman et al., "Deposition of Pressurised Aerosols in the Human Respiratory Tract", *Thorax*, 36:52–55 (1981).

Nieminen et al., "Aerosol Deposition in Automatic Dosimeter Nebulization", *Eur. J. Respir. Dis.*, 71:145–152 (1987).

Newman et al., "How Should a Pressurized $\beta$–adrenergic Bronchodilator be Inhaled?", *Eur. J. Respir. Dis.*, 62:3–21 (1981).

Adjei et al., "Pulmonary Delivery of Peptide Drugs: Effect of Particle Size of Bioavailability of Leuprolide Acetate in Healthy Male Volunteers", *Pharmaceutical Research*, 7(6):565–567.

Wearley, "Recent Progress in Protein and peptide Delivery bby Noninvasive Routes", *Critical Reviews in Therapeutic Drug Carrier Systems*, 8(4):331–392.

Moses et al., "Insulin Administered Intranasally as an Insulin–Bile Salt Aerosol", *Diabetes*, 32:1040–1047 (1983).

Salzman et al., "Intranasal Aerosolized Insulin", *New England Journal of Medicine*, 213(17):1078–1084 (1985).

Wigley et al., "Insulin Across Respiratory Mucosae by Aerosol Delivery", *Diabetes*, 20(8):552–556 (1971).

Eur. J. Respir. Dis. (1987) 71, 145–152; "Aeosol Deposition in Automatic Dosimeter Nebulization"; by Nieminen et al.

Eur. J. Respir. Dis. (1981) 62, 3–21; "How Should a Pressurized $\beta$–Adrenergic Bronchodilator be Inhaled?"; by Newman et al.

INTRAPULMONARY DELIVERY OF HORMONES

This is a continuation of application Ser. No. 08/010,989, filed Jan. 29, 1993, now abandoned to which application we claim priority under 35 USC § 120 and which application is incorporated herein in its entirety.

FIELD OF THE INVENTION

This invention relates generally to methods of administering peptides for endocrine therapy. More specifically, this invention relates to the intrapulmonary delivery of hormone drugs from a hand-held, self-contained device capable of automatically releasing a controlled amount of hormones to a patient at an optimal point in the respiratory cycle of the patient and thereafter recording the time and amount of drug delivery.

BACKGROUND OF THE INVENTION

Potent peptide hormones are available for a variety of therapeutic indications. Leuprolide, for example, is a GnRH super-agonist useful in the treatment of endometriosis and prostrate cancer. Leuprolide also has potential applications in the field of breast cancer management and the treatment of precocious puberty. Calcitonin enhances metabolism and may be a useful therapeutic agent for the management of osteoporosis, a common complication of aging.

To treat conditions or diseases of the endocrine system, pharmaceutical formulations containing potent peptide hormones are typically administered by injection. Because the stomach presents a highly acidic environment, oral preparations of peptides are unstable and readily hydrolyzed in the gastric environment. Currently, there are no oral preparations of therapeutic peptide agents available.

Both calcitonin and leuprolide can be administered nasally. (See Rizzato et al., *Curr. Ther. Res.* 45:761–766, 1989.) Both drugs achieve blood levels when introduced into the nose from an aerosol spray device. However, experiments by Adjei et al. have shown that the bioavailability of leuprolide when administered intranasally is relatively low. Adjei and Garren, *Pharmaceutical Research*, Vol. 7, No. 6, 1990.

An increase in the bioavailability of leuprolide can be obtained by administering the drug into the lung. Intrapulmonary administration of leuprolide has been shown to be an effective means of non-invasive administration of this drug. Adjei and Garren, *Pharmaceutical Research*, Vol. 7, No. 6, 1990. Intrapulmonary administration of leuprolide and other peptide drugs has the additional advantage of utilizing the large surface area available for drug absorption presented by lung tissue. This large surface area means that a relatively small amount of drug comes into contact with each square centimeter of lung parenchyma. This fact reduces the potential for tissue irritation by the drug and drug formulation. Local irritation has been seen with nasal delivery of insulin and has been a problem for commercialization of nasal preparations of that drug.

It is a problem with peptide hormones that they are very potent with effects that are not immediately manifested. For example, therapy with leuprolide for prostrate cancer does not typically produce any acute clinical effects. Similarly, prophylaxis against osteoporosis with calcitonin will not produce any acute symptoms discernible to the patient. Therefore, administration of each dose of these drugs must be reliable and reproducible. In addition, careful compliance monitoring is important to avoid therapeutic failures by carefully following the patient's adherence to the prescribed dosing regiment.

In addition, because these drugs are potent therapeutic agents, care must be taken to avoid overdosing.

The most convenient form for intrapulmonary administration of drugs by ambulatory patients is through the use of a metered dose inhaler. Metered dose inhaler devices allow the self-administration of a metered bolus of drug when the device is manually actuated by the patient during inspiration. However, such devices must be used with the proper inspiratory maneuver in order to promote effective deposition of the drug into the lung. In addition to performing a correct inspiratory maneuver, the patient must self-actuate the metered dose inhaler during the appropriate part of the inspiratory cycle. Further, when using such devices, it is not typically self-evident to the patient that the drug was properly or improperly administered. For those drugs without immediate clinical effect, the patient can easily misuse the metered dose inhaler and be under the false impression that he is correctly self-administering the drug as prescribed. Similarly, the patient may be under the false impression that he performed an incorrect inspiratory maneuver in metered dose inhaler actuation when he in fact properly performed these operations and received an appropriate amount of drug.

Devices exist to deliver metered dose inhaler drugs into the lung in a breath-actuated manner. However, such devices do not monitor the characteristics of the inspiratory breath used to trigger the device. Therefore, a sub-optimal inspiratory maneuver (e.g. one with too high of an inspiratory rate) could be used to actuate the device and produce a sub-optimal deposition pattern of drug into the lungs resulting in a sub-therapeutic blood level of the therapeutic agent being delivered.

When using a metered dose inhaler, the dosing events must be manually recorded by the patient. Many potent therapeutic hormone peptide drugs are given only once a day. It is important that the patient remember to take the prescribed daily dose, and that the dose be taken at the correct time of the day. Further, it is important that the patient not take more than the prescribed number of doses per day. The timing of delivery of potent therapeutic hormone drugs is critical because these drugs interact intimately with the chronobiology of the patient's physiology in order to produce their desired effect.

When using standard metered dose inhaler devices, the patient must manually record the time of each dosing administration. In addition, the patient must remember when to self-administer the drug. Devices exist for recording automatically metered dose inhaler drug delivery events. However, such devices do not record the presence of inspiratory flow at the time of device firing. This means that a noncompliant patient can fire the metered dose inhaler into the air and have a valid drug dosing event recorded on the self-containing recording means. In addition, the patient could self-administer the drug with an inappropriate inspiratory maneuver and have a valid drug dosing event recorded by the device. This would lead the physician to assume that the patient was compliant when, indeed, he was receiving an inappropriate amount of drug with each dosing event.

SUMMARY OF THE INVENTION

A method of treating human patients is provided by the intrapulmonary delivery of a pharmaceutically active hormone formulation. The formulation is automatically released from a hand-held, self-contained, portable device comprised of a means for automatically releasing a measured amount of drug into the inspiratory flow path of a patient in response to information obtained from a means for analyzing the inspiratory flow of a patient. Reproducible dosing is obtained by providing for automatic release in response to a measured inhalation profile. The overadministration of hormone formulations is avoided by providing a pre-programmed microprocessor designed to avoid overdosing.

It is an object of this invention to describe a method of aerosolized delivery of pharmaceutically active hormone formulation in a safe and effective manner.

An advantage of the present invention is that it can be used for ambulatory patients.

It is a feature of the invention that the device used for the aerosolized delivery of hormone formulations records the time and amount of formulation delivered.

Another advantage of the present invention is that the device used for delivering hormone formulations includes a timer which emits an audible and/or visual signal to the patient at each scheduled dosing event.

Yet another advantage of the present invention is that the method involves administering hormone formulations while simultaneously keeping an index which corresponds to the quality of the patient's inspiratory flow profile at each dosing event.

Another feature of the present invention is that when carrying out the method of delivery, a record of the date and time of each dosing event is electronically and automatically produced within a unitary device which delivers the drug.

Another advantage of the present invention is that the device presents a visual display calendar which calendar specifically indicates to the patient the day and/or time a dose was administered.

Another feature of the present invention is that the device for administering drug includes a microprocessor programmed to prevent the administration of more doses than are prescribed for the particular deficiency being treated.

Another advantage of the present invention is that better treatment protocols can be developed by the treating physician by transferring information from the delivery/recording device to a printout device which can be reviewed in order to determine the complete compliance history of the patient.

Another object of this invention is to provide an apparatus which can analyze the breathing pattern of the patient not only to determine the respiratory rate prior to delivery but also to determine the inspiratory flow profile characteristics so as to determine the optimal point in the inspiratory cycle for delivery of aerosolized hormone.

Another advantage is that the method described provides for reproducible delivery of hormones such as leuprolide wherein the reproducibility is a critical part of treatment causing each dose of hormone to have the same clinical effect.

These and other objects, advantages and features of the present invention will become apparent to those skilled in the art upon reading this disclosure in combination with drawings wherein like numerals refer to like components throughout.

BRIEF DESCRIPTION OF THE DRAWINGS

FIG. 1 is a cross-sectional view of a drug delivery device; and

FIG. 2 is a cross-sectional view of a more preferred embodiment of a drug delivery device.

DETAILED DESCRIPTION OF THE PREFERRED EMBODIMENTS

Before the present method of endocrine therapy and devices and formulations used in connection with such are described, it is to be understood that this invention is not limited to the particular methodology, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an aerosolized compound" includes a plurality of such compounds, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The terms "hormone," "hormone drug," "pharmaceutically active hormone formulation," and "peptide used in endocrine therapy" are used interchangeably herein. A hormone drug is a peptide which has been prepared in a pharmaceutically effective formulation and is useful in endocrine therapy. Specifically, a hormone drug is useful for exogenously modifying the behavior of a patient's endocrine system. Useful hormone drugs include those listed in Table 1, it being noted that peptides containing less than 50, more preferably less than 27, amino acids are preferred due to their generally smaller size. Particularly useful hormone drugs include leuprolide and calcitonin, and nafarelin.

The term "dosing event" shall be interpreted to mean the administration of hormone drug to a patient in need thereof by the intrapulmonary route of administration which event may encompass one or more releases of hormone drug formulation from an hormone drug dispensing device over a period of time of 15 minutes or less, preferably 10 minutes or less, and more preferably 5 minutes or less, during which period multiple inhalations are made by the patient and multiple doses of hormone drug are released and inhaled. A dosing event shall involve the administration of hormone drug to the patient in an amount of about 1 μg to about 10 mg in a single dosing event which may involve the release of from about 10 μg to about 100 mg of hormone drug from the device.

The term "monitoring event" shall be interpreted to mean an event taking place prior to a "dosing event" whereby the inspiratory flow of the patient's inhalation is measured in order to determine an optimal inspiratory flow rate and cumulative volume at which to allow the release of a valve so that hormone drug can be delivered to the patient. It is preferable to carry out a "monitoring event" prior to each "dosing event" so as to optimize the ability to repeatedly deliver the same amount of hormone drug to the patient at each dosing event, The term "inspiratory flow" shall be interpreted to mean a value of airflow calculated based on the speed of the air passing a given point along with the volume of the air passing that point with the volume calculation being based on integration of the flow rate data and assuming atmospheric pressure and temperature in the range of about 18° C. to about 30° C., The term "inspiratory flow profile" shall be interpreted to mean data calculated in one or more monitoring events measuring inspiratory flow rate and cumulative volume which profile can be used to determine a point within a patient's respiratory cycle which is optimal for the release of hormone drug to the patient, It is emphasized that the optimal point within the respiratory cycle for the release of hormone drug is not calculated based on a point within the cycle likely to result in the maximum delivery of hormone drug but rather the point in the cycle most likely to result in the delivery of the same amount of hormone drug to the patient at each release of hormone drug from the device,

General Methodology

A non-invasive means of endocrine therapy is provided in a manner which makes it possible to maintain tight control over the amount of drug administered to a patient, An essential feature of the invention is the intrapulmonary delivery of hormone drug to the patient in a controlled and repeatable manner, The device of the invention provides a number of features which make it possible to achieve the controlled and repeatable dosing procedure required for successful endocrine therapy. Specifically, the device is not directly actuated by the patient in the sense that no button is pushed nor valve released by the patient applying physical pressure. On the contrary, the device of the invention provides that the valve which releases hormone drug is opened automatically upon receipt of a signal from a microprocessor programmed to send a signal when data is received from a monitoring device such as an airflow rate monitoring device which measures inspiratory flow.

An important feature of the delivery device of the present invention is that the device records specific information relating to both monitoring events and dosing events and can be programmed to react to various changes in order to optimize patient treatment. Specifically, the device includes an ability to record monitoring events in order to develop an inspiratory flow profile of the patient which makes it possible to provide for greater repeatability with respect to dosing. Further, the device specifically records the time and amount of hormone drug released at each dosing event. The day and time of day of drug release is recorded. The device is equipped with a visual and audio signaling means. The audio means is programmed so as to send an audio signal when the patient is to begin a monitoring event to be followed by a dosing event. The visual display indicates specific information such as providing instructions to the patient including "conduct monitoring event" and "proceed with dosing event." Further, the visual display will indicate a calendar of days and specifically indicate on the calendar when dosing took place on the given day. Accordingly, the patient can quickly determine by visual examination whether hormone drug was delivered on any given day. It is important to administer hormone drugs at the same time each day as natural hormone release (and thus hormone administration) is closely connected to the chronobiology of the patient.

A patient using the device withdraws air from a mouthpiece and the inspiratory rate, and calculated inspiratory volume of the patient is measured one or more times in a monitoring event which determines an optimal point in an inhalation cycle for the release of a dose of hormone drug. Inspiratory flow is measured and recorded in one or more monitoring events for a given patient in order to develop an inspiratory flow profile for the patient. The recorded information is analyzed by the microprocessor in order to deduce a preferred point within the patient's inspiratory cycle for the release of hormone drug with the preferred point being calculated based on the most likely point to result in a reproducible delivery event.

The flow rate monitoring device continually sends information to the microprocessor, and when the microprocessor determines that the optimal point in the respiratory cycle is reached, the microprocessor actuates the opening of the valve allowing release of hormone drug. Accordingly, drug is always delivered at a pre-programmed place in the inspiratory flow profile of the particular patient which is selected specifically to maximize reproducibility of drug delivery and peripheral deposition of the drug. It is pointed out that the device of the present invention can be used to, and actually does, improve the efficiency of drug delivery. However, this is not the critical feature. The critical feature is the reproducibility of the release of a tightly controlled amount of drug at a particular point in the respiratory cycle so as to assure the delivery of a controlled and repeatable amount of drug to the lungs of each individual patient.

The combination of automatic control of the valve release, combined with frequent monitoring events in order to calculate the optimal flow rate and time for the release of hormone drug, combine to provide a repeatable means of delivering hormone drug to a patient. Because the valve is released automatically and not manually, it can be predictably and repeatedly opened for the same amount of time each time or for the preprogrammed measured amount of time which is desired at that particular dosing event. Because dosing events are preferably preceded by monitoring events, the amount of hormone drug released and/or the point in the inspiratory cycle of the release can be readjusted based on the particular condition of the patient. For example, if the patient's breathing pattern at rest changes, e.g., after exercise, such will be taken into account in the monitoring event by the microprocessor which will readjust the amount and/or point of release of the hormone drug in a manner calculated to provide for the administration of the same amount of hormone drug to the patient at each dosing event.

It has been found that the ability to tightly control the amount of a volatile propellant formulation of drug delivered via the intrapulmonary route can be improved by delivering smaller doses of the propellant/drug formulation with each release of the valve and with each dosing event. Repeatability, in terms of the amount of hormone drug delivered to a patient, is improved when the hormone drug is delivered during a smooth, normal inhalation by the patient. To a certain extent, the ability to provide for a smooth inhalation is enhanced when smaller amounts of hormone drug are released as compared with larger amounts of hormone drug. Accordingly, an important aspect of the invention is to deliver aerosolized hormone drug to a patient in a series of interrupted bursts while the patient continues a single inhaled breath, with each burst being delivered while the patient maintains optimal inspiratory flow.

Short bursts of the release of hormone drug can be obtained as two or more bursts but are preferably three or four bursts. The amount of time the valve is opened is generally in the range of about 0.05 seconds to 1 second but is more preferably 0.1 seconds to 0.25 seconds. When the hormone drug is being released in a series of short bursts, it is preferable for the valve to be open a substantially shorter period of time than the valve is closed. For example, the valve might be opened for approximately 0.1 seconds and closed for approximately 0.5 seconds, followed by another opening of 0.1 seconds and another closing of 0.5 seconds, with this pattern being repeated a plurality of times. Repeatability and dosing can be improved by providing for four bursts, wherein each burst allows for the valve to be opened four times, separated by three closings, wherein the amount of closed time is two to eight times longer than the amount of open time for each on/off event. Particularly preferred repeatability can be obtained by allowing for four bursts, wherein the valve is opened for approximately 0.015 seconds, followed by a closing for approximately 0.1 second, which pattern is repeated for four openings, separated by three closings.

The amount of hormone drug delivered to the patient will vary greatly depending on the particular drug being delivered. In accordance with the present invention it is possible to deliver a wide range of different hormone drugs. The drugs must pass through pulmonary membranes and, as such, are preferably small—less than 50 amino acids, more preferably, less than 27 amino acids, in size. The most preferred drugs include leuprolide and calcitonin. Hormone drugs are generally administered to a patient in an amount in the range of about 10 μg–100 μg. Useful hormones are listed below in Table 1.

TABLE 1

Useful Peptide Hormone Drugs

| Compound | Amino acids |
|---|---|
| Somatostatin | 6 |
| Oxytocin | 9 |
| Desmopressin | 9 |
| LHRH | 10 |
| Nafarelin | 10 |
| Leuprolide | 11 |
| ACTH analog | 17 |
| Secretin | 27 |
| Glucagon | 29 |
| Calcitonin | 32 |
| GHRH | 40 |
| Growth hormone | 191 |

These doses are based on the assumption that when intrapulmonary delivery methodology is used the efficiency of the delivery is approximately 10% and adjustments in the amount released must be made in order to take into account the efficiency of the device. The differential between the amount of hormone drug actually released from the device and the amount of hormone drug actually delivered to the patient varies due to a number of factors. In general, the present device is approximately 20% efficient, however, the efficiency can be as low as 10% and as high as 50% meaning that as little as 10% of the released hormone drug may actually reach the circulatory system of the patient and as much as 50% might be delivered. The efficiency of the delivery will vary somewhat from patient to patient and must be taken into account when programming the device for the release of hormone drug. In general, a conventional metered dose inhaling device is about 10% efficient.

When administering hormone drug using the inhalation device of the present invention, the entire dosing event can involve the administration of anywhere from 1 μg to 100 mg, but more preferably involves the administration of approximately 10 μg to 10 mg. The large variation in the amounts which might be delivered are due to the fact that different drugs have greatly different potencies and may be delivered from devices which vary greatly in terms of the efficiency of drug delivered. The entire dosing event may involve several inhalations by the patient with each of the inhalations being provided with multiple bursts of hormone drug from the device. For example, the device can be programmed so as to release enough hormone drug so that approximately 1 mg of hormone drug is delivered to the patient per inhalation or 0.33 mg of hormone drug per burst with three bursts being delivered per inhalation. If ten mg are to be delivered, the ten mg are delivered by releasing 33 bursts in ten different inhalations. Such a dosing event should take about 1–2 minutes to deliver 10 mg of hormone drug. Since only small amounts are delivered with each burst and with each inhalation, even a complete failure to deliver hormone drug with a given inhalation or burst is not of great significance and will not seriously disturb the reproducibility of the dosing event. Further, since relatively small amounts are delivered with each inhalation and/or burst, the patient can safely administer a few additional milligrams of hormone drug without fear of overdosing.

In addition to drug potency and delivery efficiency, hormone drug sensitivity must be taken into consideration. The present invention makes it possible to vary dosing over time if hormone sensitivity changes and/or if user compliance and/or lung efficiency changes over time.

Based on the above, it will be understood that the dosing or amount of hormone drug actually released from the device can be changed based on the most immediately prior monitoring event wherein the inspiratory flow of a patient's inhalation is measured.

The dosing program can be designed with some flexibility. For example, if the patient normally requires 25 mg per day of hormone drug, the microprocessor of the inhalation device can be programmed to prevent further release of the valve after 35 mg have been administered within a given day. Setting a slightly higher limit would allow for the patient to administer additional hormone drug, if needed, due to misdelivery of hormone drug such as due to coughing or sneezing during an attempted delivery.

The ability to prevent overdosing is a characteristic of the device due to the ability of the device to monitor the amount of hormone drug released and calculate the approximate amount of hormone drug delivered to the patient based on monitoring given events such as the respiratory rate, The ability of the present device to prevent overdosing is not merely a monitoring system which prevents further manual actuation of a button. As indicated above, the device used in connection with the present invention is not manually actuated, but is fired (i.e., drug released) in response to an electrical signal received from a microprocessor (which received data from a monitoring device such as a device which monitors inspiratory flow) and allows the actuation of the device upon achieving an optimal point in a inspiratory cycle. When using the present invention, each release of the valve is a release which will administer drug to the patient in that the valve is released in response to patient inhalation. More specifically, the device does not allow for the release of hormone drug merely by the manual actuation of a button to fire a burst of hormone drug into the air or a container.

The microprocessor of applicant's invention will also include a timing device. The timing device can be electrically connected with visual display signals as well as audio alarm signals. Using the timing device, the microprocessor can be programmed so as to allow for a visual or audio signal to be sent when the patient would be normally expected to administer hormone drug. In addition to indicating the time of administration (preferably by audio signal), the device can indicate the amount of hormone drug which should be administered by providing a visual display. For example, the audio alarm could sound alerting the patient that hormone drug should be administered. At the same time, the visual display could indicate "50 µg" as the amount of hormone drug to be administered. At this point, a monitoring event could take place. After completion of the monitoring event, administration would proceed and the visual display would continually indicate the remaining amount of hormone drug which should be administered. After the predetermined dose of 50 µg had been administered, the visual display would indicate that the dosing event had ended. If the patient did not complete the dosing event by administering the stated amount of hormone drug, the patient would be reminded of such by the initiation of another audio signal, followed by a visual display instructing the patient to continue administration.

Additional information regarding dosing with hormone drug via injection can be found within Wearley, L. L., "Recent Progress in Protein and Peptide Delivery by Noninvasive Router," *Critical Reviews in Therapeutic Drug Carrier Systems*, 8(4):331–394 (1991) and Harrison's—*Principles of Internal Medicine* (most recent edition) published by McGraw Hill Book Company, New York, incorporated herein by reference to disclose information regarding the dosing of hormone drugs.

Delivery Device

Figure 2:
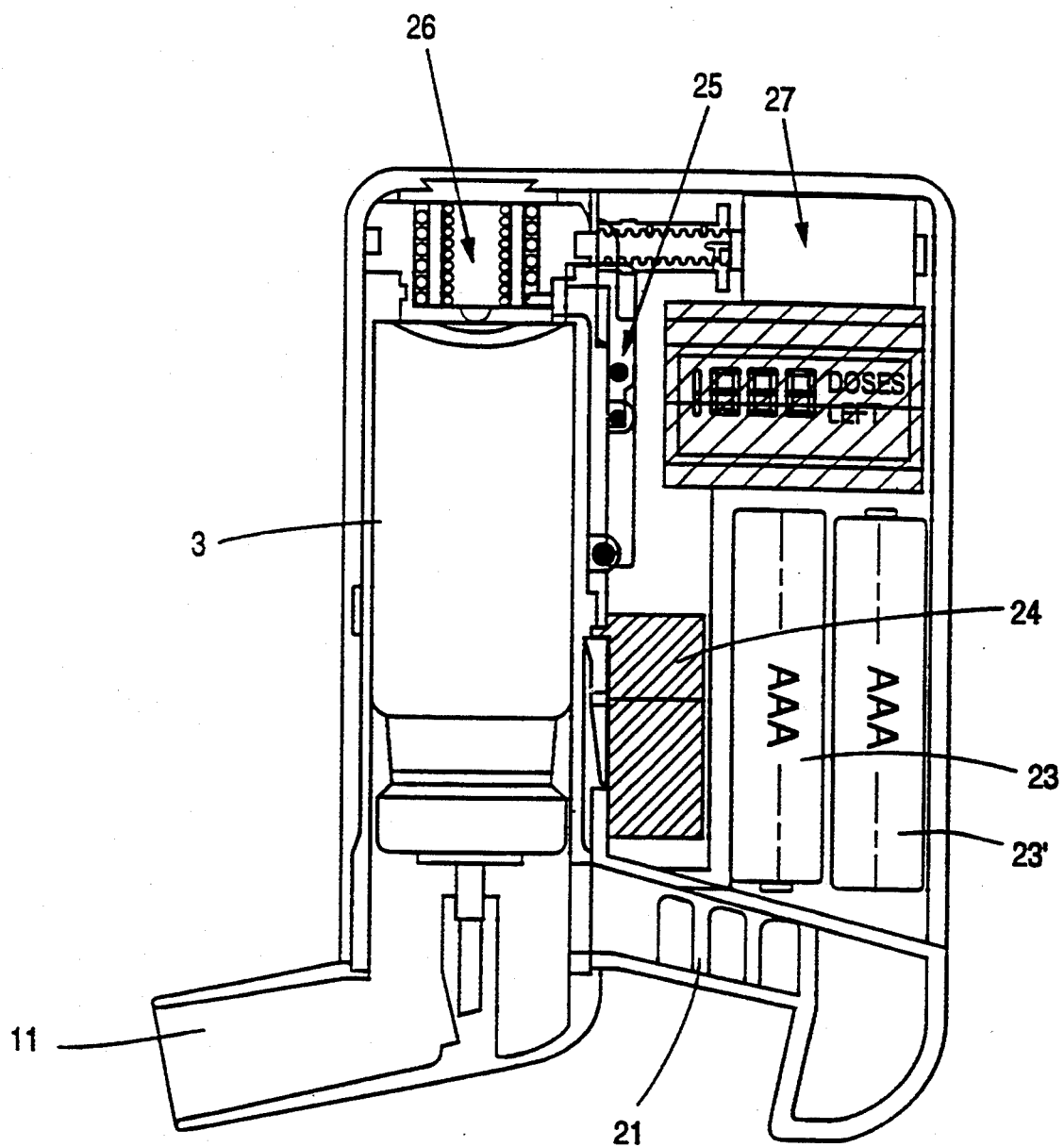

Before referring to the specific embodiments of the delivery device shown in FIGS. 1 and 2, an explanation will be provided regarding a general mechanism which can be used in connection with the method of intrapulmonary administration of hormones. Such a device is a hand-held, portable device which is comprised of (a) a means for analyzing the inspiratory flow of a patient and (b) a means for automatically releasing a measured amount of a hormone into the inspiratory flow path of a patient, e.g. an automatic valve actuation means. In order to use the device, the device must be "loaded", i.e. connected to (c) a source of hormone drug which, in general, is a potent hormone drug suspension dispersed within a low boiling point propellant. The entire device is light weight (less than 1 kg loaded) and portable.

A formulation of hormone drug in a low boiling point propellant is typically contained in a pressurized canister which is connectable to the "unloaded" device, i.e., the device without the container. When the container of propellant and hormone drug is connected to the device, the container will include a valve opening at one end which opening is seated into a flow path within the device. The device preferably includes a mouth piece at the end of the flow path, and the patient inhales from the mouth piece which causes an inspiratory flow to be measured within the flow path. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means. When the actuation means is signaled, it releases a valve allowing hormone drug and propellant to escape into the inspiratory flow path of the device and ultimately into the patient's lungs. After being released, the drug and propellant will preferably pass through a nozzle prior to entering the inspiratory flow path of the device and thereafter the lungs of the patient.

It is important to note that the firing threshold of the device is not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume when it determines the optimal point in the patient's inspiratory cycle which would be most preferable in terms of reproducibly delivering the same amount of drug to the patient with each release of drug. Further, the device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time.

FIG. 1 shows a cross-sectional view of a hand-held, portable, electronic breath-actuated inhaler device which can be used in connection with the present invention. The device is shown with a holder 1 having cylindrical side walls and a removable cap. The holder 1 is "loaded" in that it includes the pressurized canister 3. The canister 3 includes a non-metering valve 5 which is held down in the open position when the cap 2 is screwed down, thus setting the valve 5 into a seat 6 which is in connection with a flow path 8.

A formulation 4 comprised of a hormone such as leuprolide or calcitonin and a suitable propellant, such as a low boiling point propellant, is contained within the pressurized canister 3. Propellant and hormone drug are released from the canister 3 via the electrically controlled solenoid 7. In that the valve 5 of the canister is continuously open, another valve, contained within solenoid 7, facilitates the release of the drug. When the solenoid 7 allows release of propellant and drug, the propellant and drug flows through the flow path 8 and then through the solenoid actuated valve 9 into the flow path 10, out through the nozzle 13 and then into the inspiratory flow path 11 surrounded by walls 12.

It is important to note that a variety of devices can be used in order to carry out the endocrine therapy of the present invention. However, the device must be capable of allowing the release of a metered amount of hormone drug based on pre-programmed criteria which are readable by the microprocessor 22. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 22, containing read only memory which in turn contains the pre-programmed information, is plugged into the device. For each of these three embodiments, changing the programming of the memory device readable by microprocessor 22 will radically change the behavior of the device by causing microprocessor 22 to be programmed in a different manner. As regards the present invention, the non-volatile memory contains information relevant only to the administration of a specific hormone drug such as leuprolide. Microprocessor 22 sends signals to solenoid 7 which determines the amount of drug delivered into the inspiratory flow path. Further, microprocessor 22 keeps a record of all drug dosing times and amounts using a read/write non-volatile memory which is in turn readable by an external device. The formulation 4 contained within canister 3 is released into the atmosphere ultimately via nozzle 13 which opens into inspiratory flow path 11. It is at this point that the low boiling point propellant within formulation 4 flashes, i.e. rapidly evaporates, thus providing particles of hormone drug in an aerosol which is introduced into the mouth and ultimately into the lungs of the patient. In order to allow for ease of use, it is possible to form inspiratory flow path 11 into a mouth piece which can be specifically designed to fit the mouth of a particular patient using the device.

In place of the mouthpiece referred to above, it is possible to design the flow path 11 so as to include one or two smaller tubes which can fit within the nostrils or a "nose mask"-like covering which encompasses the nostril openings. By designing the end of the flow path 11 in this manner, it is possible to provide for nasal delivery. Using this technique, the hormone drug is delivered by transmucosal permeation and is not generally inhaled into the lungs. Requiring a minimal nasal inspiratory flow prior to firing ensures that nasal congestion is not present which might be exacerbated by drug delivery. Other features of the invention remain the same. In particular, the day and time of day of each monitoring and dosing event is recorded within the device and the patient is signalled regarding the time and the amount of drug to be delivered at each dosing event which information is also recorded. However, in accordance with such a methodology, it is important to take into consideration the differences in efficiency between intrapulmonary and nasal delivery. Dosing adjustments can be made by those skilled in the art by delivering small doses at first and continually increasing the dosage amount while continuing to monitor blood levels of the delivered hormone drug in order to determine what dosing amounts deliver the required amount of hormone drug to carry out appropriate endocrine therapy. Information regarding the bioavailability of certain hormone drugs by nasal delivery is provided below in Table 2.

TABLE 2

Intranasal Bioavailabilities of Proteins and Peptides

| Compound | Amino acids | Bioavailability (%) |
|---|---|---|
| Somatostatin | 6 | 75 |
| Oxytocin | 9 | 1 |
| Desmopressin | 9 | 10 |
| LHRH | 10 | 1.5 |
| Nafarelin | 10 | 2 |
| Leuprolide | 11 | <10 |
| ACTH analog | 17 | 12 |
| Secretin | 27 | 10 |
| Glucagon | 29 | <1 |
| Calcitonin | 32 | <1 |
| GHRH | 40 | <1 |
| Growth hormone | 191 | <1 |

The solenoid 7, and associated valve 9, flow paths 8 and 10, as well as nozzle 13 make up the aerosol delivery system 14 shown by the dotted lines within FIG. 1. The system 14 is in connection with the flow sensor 15 which is capable of measuring a flow rate of about 0 to about 300 liters per minute. The flow sensor 15 includes screens 16, 17 and 18 which are positioned approximately $\frac{1}{4}''$ apart from each other. Tubes 19 and 20 open to the area between the screens 16, 17 and 18 with the tubes 19 and 20 being connected to a conventional differential pressure transducer 21. When the user draws air through inspiratory flow path 11, air is passed through the screens 16, 17 and 18 and the air flow can be measured by the differential air pressure transducer 21. The flow sensor 15 is in connection with the aerosol delivery system 14, and when a threshold value of air flow is reached, the aerosol delivery system 14 allows the release of formulation 4 so that a controlled amount of hormone drug is delivered to the patient. Solenoid 7 is connected to a microprocessor 22 via an electrical connection. The details of the microprocessor and the details of other drug delivery devices which might be used in connection with the present invention are described and disclosed within US patent application Ser. No. 07/664,758, filed on Mar. 5, 1991 entitled "Delivery of Aerosol Medications for Inspiration," which application is incorporated in its entirety herein by reference, and it is specifically incorporated in order to describe and disclose devices as shown within FIG. 1 and the microprocessor and program technology used therewith.

A cross-sectional view of yet another (and more preferred) embodiment of the hand-held, electronic, breath-actuated inhaler device of the invention is shown in FIG. 2. The device of FIG. 2 shows all of the components present within the single hand-held, portable device, i.e. the power source not shown in FIG. 1 is shown in the device in FIG. 2. Like the device shown within FIG. 1, the device of FIG. 2 includes a canister 3 which includes a canister valve 5. However, unlike the device of FIG. 1, the device of FIG. 2 does not have the valve continuously open but allows a valve 5 connected to the canister 3 to be opened by the mechanical force generated by a valve actuation mechanism 26 which is a motor driven, mechanical mechanism powered by a power source such as batteries 23 and 23'. However, like the device shown within FIG. 1, the patient inhales through inspiratory flow path 11 which can form a mouth piece in order to obtain a metering event using the differential pressure transducer 21. Further, when the inspiratory flow meets a threshold of a pre-programmed criteria, the microprocessor 24 sends a signal to an actuator release mechanism 25 which actuates the actuation mechanism 26 forcing canister 3 downward so that canister valve 5 releases formulation into the inspiratory flow path 11. Further details regarding the device of FIG. 2 are described within co-pending US patent application entitled "An Aerosol Medication Delivery System and Methods," filed on Jan. 29, 1993 as Ser. No. 08/002,507, which application is incorporated herein by reference in its entirety and specifically incorporated in order to describe and disclose devices as shown within FIG. 2 and the microprocessor and program technology used therewith.

Microprocessor 24 of FIG. 2 includes an external non-volatile read/write memory subsystem, peripheral devices to support this memory system, reset circuit, a clock oscillator, a data acquisition subsystem and an LCD annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of hormone drug to a patient upon actuation. Adjustments can be made in the program so that when the patient's inspiratory flow profile is changed such is taken into consideration. This can be done by allowing the patient to inhale through the device as a test in order to measure air flow with preferred drug delivery points determined based on the results of several inhalations by each particular patient. This process can be readily repeated when the inspiratory flow profile is changed for whatever reason, e.g., abdominal incisional pain resulting in low tidal volumes. Determination of optimal drug delivery points in the inspiratory flow can be done at each dosing event, daily, weekly, or with the replacement of a new canister in the device.

The microprocessor of the present invention, along with its associated peripheral devices, can be programmed so as to prevent the release of drug from the canister from occurring more than a given number of times within a given period of time. This feature makes it possible to prevent overdosing the patient with a potent hormone. The overdose prevention feature can be particularly designed with each individual patient in mind or designed with particular groups of patients in mind. For example, the microprocessor can be programmed so as to prevent the release of more than approximately 200 µg of leuprolide per day when the patient is normally dosed with approximately 100 µg of leuprolide per day. The systems can also be designed so that only a given amount of a particular hormone drug is provided at a given dosing event. For example, the system can be designed so that only approximately 100 µg of leuprolide is given in a given 15-minute period over which the patient will make approximately 10 inhalations with 10 µg of leuprolide being delivered with each inhalation. By providing this feature, greater assurances are obtained with respect to delivering the hormone drug gradually over time and thereby providing controlled endocrine therapy without overdosing the patient.

Another feature of the device is that it may be programmed to not release drug if it does not receive a signal transmitted to it by a transmitter worn by the intended user. Such a system improves the security of the device and prevents abuse by unauthorized users.

The microprocessor of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. All of the features of the invention are provided in a portable, programmable, battery-powered, hand-held device for patient use which has a size which compares favorably with existing metered dose inhaler devices.

The microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the valve when the inhalation cycle is repeated during the dosing event. The devices of FIGS. 1 and 2 have been put forth in connection with devices which use a low boiling point propellant and preferably use that propellant in combination with a suspension formulation which includes the dry powdered hormone drug within the low-boiling-point propellant. Those skilled in the art will readily recognize that such devices can be used for administering a solution of hormone drug within the low-boiling-point propellant. However, those skilled in the art will also readily recognize that different mechanisms will be necessary in order to deliver different formulations, such as a dry powder without any propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation would then cause the dry powder to form a dry dust cloud and be inhaled. Dry powder can also be aerosolized by compressed gas, and a solution can be aerosolized by a compressed gas released in a similar manner and then inhaled.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

I claim:

1. A method of endocrine therapy by intrapulmonary administration of a peptide drug used in endocrine therapy, comprising:

measuring inspiratory flow of a patient and calculating a point in an inhalation cycle of the patient based on measuring inspiratory flow of a patient and calculating a point in an inhalation cycle of the patient based on
(a) a measured inspiratory flow rate; and
(b) measured cumulative inspiratory volume;

releasing, at the calculated point a metered dose of aerosolized peptide drug from a pressurized canister containing peptide drug in combination with a low boiling point propellant;

inhaling the metered dose of aerosolized peptide drug in the patient's lungs;

repeating the measuring, releasing and inhaling in a manner such that the releasing occurs each time at the same (a) measured inspiratory flow rate, and (b) measured inspiratory volume so as to obtain repeatability in dosing and so as to maintain a desired drug to blood ratio in the patient; and recording the day, time and amount of each release of aerosolized drug;

wherein the measuring, releasing and inhaling are carried out with a unitary, hand-held device.

2. The method of claim 1, wherein the releasing is carried out after the device sends an audio signal to the patient.

3. The method of claim 2, wherein the releasing is automatically carried out by sending an electronic signal to a valve actuation means which opens a valve in response to a received electronic signal.

4. The method of claim 1, wherein the peptide drug is leuprolide.

5. The method of claim 1, wherein the peptide drug is selected from the group consisting of somatostatin, oxytocin, desmopressin, LHRH, nafarelin ACTH analog, secretin glucagon, calcitonin, GHRH, leuprolide, interferon-$\beta$ and growth hormone.

6. The method as claimed in claim 1, wherein the amount of peptide drug administered and the respiratory rate monitored are continually recorded and adjustments are made in the amount of drug administered based on the effect of drug administration on the level of peptide drug in the patient's blood.

7. The method as claimed in claim 1, wherein the peptide drug is administered in an amount in the range of from about 1 $\mu$g to about 4 mg.

8. The method as claimed in claim 7, wherein the peptide drug is leuprolide.

9. The method as claimed in claim 7, wherein the peptide drug is selected from the group consisting of somatostatin, oxytocin, desmopressin, LHRH, nafarelin ACTH analog, secretin glucagon, calcitonin, GHRH, leuprolide, interferon-$\beta$ and growth hormone.

10. The method as claimed in claim 1, further comprising:
retrieving the recorded information regarding the time and amount of peptide drug administered.

11. The method of claim 10, further comprising:
analyzing the retrieved information to determine desired dosing levels for further administration of peptide drug to the patient.

12. The method of claim 11, wherein the drug is calcitonin.

13. The method of claim 1:
wherein the measuring is carried out immediately prior to releasing the peptide drug.

* * * * *